United States Patent
Stone et al.

(10) Patent No.: US 7,252,832 B1
(45) Date of Patent: Aug. 7, 2007

(54) COMPOSITE COLLAGEN MATERIAL AND METHOD OF FORMING SAME

(75) Inventors: Kevin T. Stone, Winona Lake, IN (US); Karen Troxel, Warsaw, IN (US)

(73) Assignee: Biomet Sports Medicine, Inc., Warsaw, IN (US)

( * ) Notice: Subject to any disclaimer, the term of this patent is extended or adjusted under 35 U.S.C. 154(b) by 0 days.

(21) Appl. No.: 11/010,836

(22) Filed: Dec. 13, 2004

(51) Int. Cl.
  *A61F 13/00* (2006.01)
(52) U.S. Cl. ..................................................... 424/422
(58) Field of Classification Search ................ 530/350; 623/13.17
  See application file for complete search history.

(56) References Cited

U.S. PATENT DOCUMENTS

| | | | |
|---|---|---|---|
| 4,772,288 A | 9/1988 | Borner et al. | |
| 4,834,734 A * | 5/1989 | Morganti | .............. 604/368 |
| 5,067,964 A | 11/1991 | Richmond et al. | |
| 5,078,744 A | 1/1992 | Chvapil | |
| 5,458,636 A | 10/1995 | Brancato | |
| 5,782,915 A | 7/1998 | Stone | |
| 6,050,979 A * | 4/2000 | Haemmerle et al. | .............. 604/265 |
| 6,537,313 B2 | 3/2003 | Ketharanathan | |
| 2003/0212456 A1 | 11/2003 | Lipchitz et al. | |
| 2004/0034418 A1 | 2/2004 | Li et al. | |

OTHER PUBLICATIONS

Cohn et al., Cardiac Surgery in the Adult, (New York:McGraw-Hill), 2003:15271536: Chapter 65, "Tissue engineering for cardiac surgery." See p. 9.*

* cited by examiner

*Primary Examiner*—Karen Cochrane Carlson
*Assistant Examiner*—Agnes B. Rooke
(74) *Attorney, Agent, or Firm*—Harness, Dickey & Pierce, PLC

(57) ABSTRACT

A felt for repairing soft tissue defects comprising a membranous collagen substrate and a bioresorbable fiber felted onto the collagen substrate. Methods of preparing a felt and methods of repairing soft tissue damage with a felt are also provided.

18 Claims, 4 Drawing Sheets

COMPOSITE COLLAGEN MATERIAL AND METHOD OF FORMING SAME

FIELD OF THE INVENTION

The present invention relates to composite collagen materials. More particularly, the present invention relates to a composite collagen felt used for soft tissue repair.

BACKGROUND OF THE INVENTION

Collagen is useful in various pharmaceutical applications and as an implant material for soft tissue defects. The collagen useful for implant materials may be broadly categorized into xenograft collagen and allograft collagen. Selecting the appropriate collagen materials may present challenges as there is a need to balance strength and durability of the implant with reducing immunogenicity and promoting soft tissue ingrowth.

It may be desirable to provide an implant which promotes soft tissue ingrowth, minimizes the amount of the implant used, and is not prone to an immunogenic response.

SUMMARY OF THE INVENTION

Embodiments of the present invention relate to felts for repairing soft tissue defects comprising a collagen substrate and a bioresorbable material felted onto the collagen substrate. The collagen substrate may be selected from a xenograft source, an allograft source, or a synthetic source. The collagen substrate may be from a porcine source. The collagen substrate may be uncrosslinked, partially crosslinked, or fully crosslinked. Chemical crosslinking may be introduced in an amount sufficient to make the collagen substantially non-bioactive. Bioresorbable materials may be selected from synthetic polymers, natural polymers, polysaccharides, and mixtures thereof. Synthetic polymers may include polymers and copolymers of glycolic acid, L-lactic acid, D-lactic acid, urethane urea, trimethylene carbonate, dioxanone, caprolactone, hydroxybutyrate, orthoesters, orthocarbonates, aminocarbonates, and physical combinations thereof. Natural polymers may include collagen, elastin, silk, fibrin, fibrinogen, or other naturally occurring tissue-derived proteins. Natural polysaccharides may include hyaluronic acid, chitin, chitosan, alginate, carboxymethylcellulose, or other polysaccharides. The felt may be substantially planar. The felt may also have nutrient factors, growth factors, antimicrobials, anti-inflammatory agents, blood products, autologous or allogeneic differentiated cells, autologous or allogeneic undifferentiated or stem cells, and mixtures thereof incorporated into the felt. Cartilage implants, ligament implants, or tendon implants are examples of what may be made with the felt.

Various embodiments of the present invention provide methods of preparing a felt, comprising providing a membranous collagen substrate and felting a bioresorbable polymer onto the substrate. The collagen substrate may be uncrosslinked, partially crosslinked, or fully crosslinked. Crosslinking of the collagen substrate may be performed using chemical crosslinking, UV radiation, dehydrothermal crosslinking, and combinations thereof. Chemical crosslinking agents may include carbodiimide, glutaraldehyde, formaldehyde, diisocyanates, and mixtures thereof. Felting may further comprise passing a barbed needle through the bioresorbable polymer and the collagen substrate to pass the bioresorbable polymer through at least one surface of the collagen substrate. A sterilization step may also be performed on the felt after the felting process. The felt may also be treated with nutrient factors, growth factors, antimicrobials, anti-inflammatory agents, blood products, autologous or allogeneic differentiated cells, autologous or allogeneic undifferentiated or stem cells, and mixtures thereof.

Various embodiments of the present invention also provide methods of augmenting a site in need of soft tissue repair, comprising: providing a felt, comprising a membranous collagen substrate and a bioresorbable polymer fiber felted onto the substrate and placing the felt at the site in need of tissue repair. The felt may be shaped appropriately, if needed, and affixed to the site in need of tissue repair.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

The following description of the preferred embodiment(s) is merely exemplary in nature and is in no way intended to limit the invention, its application, or uses. Although various embodiments may be illustrated in conjunction with a shoulder, elbow, or finger, it is understood that the felt and methods of the invention may be of any appropriate shape and may be used with any appropriate procedure and not solely those illustrated.

Figure 1:
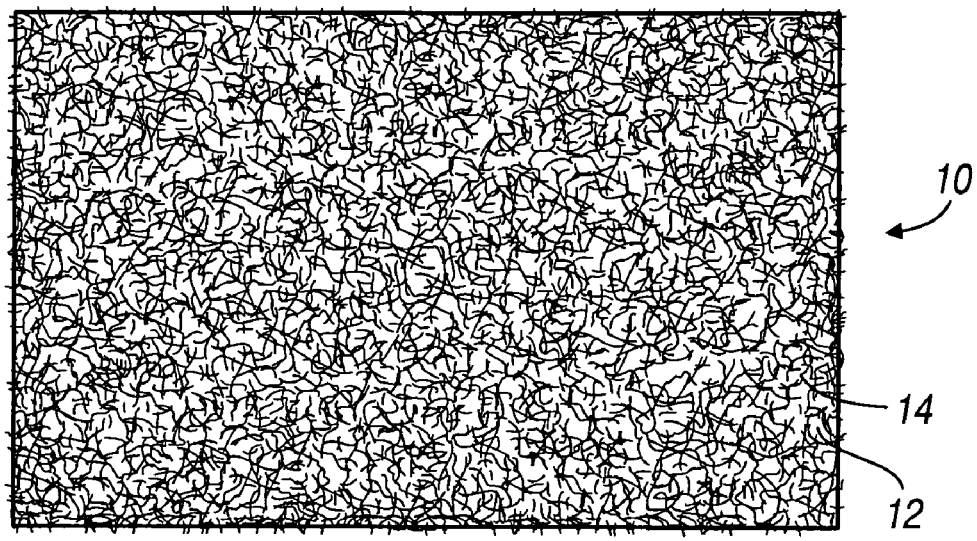
FIG. 1 depicts a felt according to embodiments of the present invention.
Figure 2:
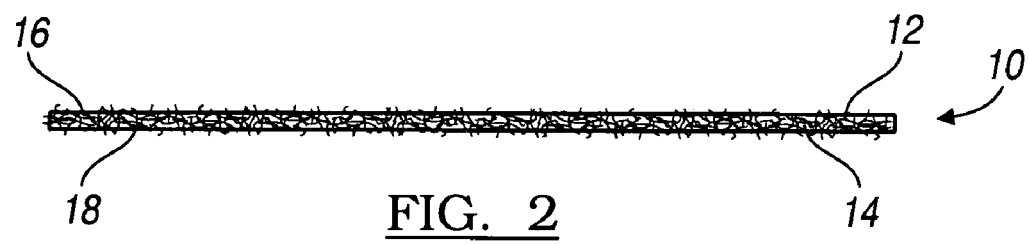
FIG. 2 depicts a cut away view of a felt according to embodiments of the present invention.

As depicted in FIGS. 1 and 2, a felt 10 comprises a membranous collagen substrate 12 and a bioresorbable polymer 14 felted onto the substrate 12. The membranous collagen may be naturally derived from tissue such as submucosal intestine, or may be fabricated by casting a collagen solution into a membrane. The collagen substrate 12 may be from a xenograft source, an allograft source, or a synthetic source. For example, a porcine collagen may be used for the collagen substrate 12. Porcine collagen is readily available, provides flexibility of the collagen substrate 12, and is durable. Depending on the end use of the felt, the collagen substrate 12 may be from any collagen source (e.g. human, porcine, or bovine) which provides the desired durability, flexibility and permanence.

The collagen substrate 12 may uncrosslinked (0% linkages), partially crosslinked (greater than 0% and less than 100% linkages), or fully crosslinked (100% linkages). The collagen substrate 12 may be sufficiently crosslinked to be substantially non-resorbable and non-bioactive. One skilled in the art appreciates that the non-resorbtion or permanency of the collagen substrate 12 increases with the amount of crosslinked bonds. For example, in a highly crosslinked collagen substrate 12 having 85% crosslinked bonds, the collagen substrate 12 may remain implanted and substantially intact inside of a recipient for months, decades, or a lifetime. Furthermore, the high percentage of crosslinked bonds may ensure that the substantial majority of the collagen substrate 12 does not degrade, deform, or otherwise lose strength over the life of the implanted felt 10. In contrast, a lesser crosslinked collagen substrate 12 having about 10% linkage, may be for temporary use and designed to retain the majority of its structural integrity for only a few weeks or months. This may be useful in less load bearing areas of the body or in situations where the repair is minor and may be replaced with regenerated tissue in a short time period.

The bioresorbable polymer 14 may be a synthetic polymer, a natural polymer, polysaccharides, and mixtures thereof. Synthetic bioresorbable materials may include, but are not limited to, polymers and copolymers of glycolic acid, L-lactic acid, D-lactic acid, urethane urea, trimethylene carbonate, dioxanone, caprolactone, hydroxybutyrate, orthoesters, orthocarbonates, aminocarbonates, and physical combinations thereof. Other polymerizable hydroxy acids may also be employed. Synthetic resorbable materials may provide control in the amount of the material used as the benefits and delivery rates of the resorbable material 14 may be calculated based on known dissolution rates of the polymer. The bioresorbable polymer 14 may also be a natural polymer such as collagen, elastin, silk, fibrin, fibrinogen, other naturally occurring tissue-derived proteins, and mixtures thereof. Natural polysaccharides may include, without limitation, hyaluronic acid, chitin, chitosan, alginate, carboxymethylcellulose, other polysaccharides, and mixtures thereof. The bioresorbable polymer 14 collagen may be of the same or a different type or strength as the collagen substrate 12.

The bioresorbable polymer 14 may be a fluffy batting or web of threads of the linked monomers or the collagen. The fluffy batting forms a felt or dense cover over at least one of a top surface 16 and/or a bottom surface 18 of the collagen substrate 12. The dense cover may be of a random orientation or in a patterned form. The felt 10 may also include combinations of random and patterned orientations. The bioresorbable polymer 14 may be tightly felted to the surface of the collagen substrate 12 such that the fibers are touching or there is minimal space between each of the intertwined fibers. The tightness of the felt 10 may also be modified by having the bioresorbable polymer 14 fibers abut the top surface 16 and bottom surface 18 of the collagen substrate 12. The close fit between the bioresorbable polymer 14 and the collagen substrate 12 makes the felt 10 appear substantially planar when viewed from the side, as depicted in FIG. 2. The tightness of the felt 10 may be adjusted to incorporate additional elements into the substrate 12 or into the substrate 12 and the web of the bioresorbable polymer 14 such as autologous or allogeneic differentiated cells, autologous or allogeneic undifferentiated or stem cells and other biological agents, such as nutrient factors, growth factors, antimicrobials, anti-inflammatory agents, blood products, and mixtures thereof.

The bioresorbable polymer 14 resorbs faster than the collagen substrate 12 and elicits a positive tissue response to make newly generated tissues develop into the collagen substrate 12. The selection of bioresorbable polymers 14 may enhance the healing process. For example, it may be desirable to incorporate 65% of a slowly resorbing polymer 14 and 35% of rapidly resorbing polymer 14. The presence of the slowly resorbing polymer 14 may be used to enhance the strength of the felt 10 because the rapidly resorbing polymer 14 would initially elicit a tissue ingrowth response until it completely dissolved at which time the slowly resorbing polymer 14 would continue to promote ingrowth. The slowly resorbing polymer 14 may also provide enhanced strength to the felt 10 for a longer duration than a felt 10 containing a single bioresorbable polymer 14 or multiple bioresorbable polymers 14 having the same resorbtion rates.

Embodiments of the present invention also provide methods of preparing the felt 10. A membranous collagen substrate 12 is provided. The collagen may be uncrosslinked or partially or fully crosslinked using, for example, chemical crosslinking, UV radiation, dehydrothermal crosslinking, and combinations of these treatments. Chemical crosslinking may be performed using a chemical crosslinking agent, including, but not limited to, carbodiimide, glutaraldehyde, formaldehyde, diisocyanates, and mixtures thereof. The crosslinking is carried out for a time and under conditions sufficient to provide a non-immunogenic collagen substrate 12. In embodiments where a greater degree of crosslinking is desired, the duration of the crosslinking treatment may increase or a successive series of crosslinking treatments (UV radiation followed by carbodiimide treatment, for example) may be used.

The felting process consists of using a barbed needle to pass the bioresorbable polymer 14 through a portion the collagen substrate 12. The barbs in the needle catch nearby bioresorbable polymer 14 fibers and mix, interlock, or weave them with other fibers to form the dense cover felt. The bioresorbable polymer 14 may be placed on the top surface 16, bottom surface 18, or both surfaces of the collagen substrate 12 to facilitate the felting process. The needle punches the bioresorbable polymer 14 through the top surface 16, into the collagen substrate 12, through the bottom surface 18, and back through the collagen substrate 12, or vice versa. The needle may also punch the resorbable polymer 14 through only a single surface of the collage substrate 12 without engaging the opposing surface. Repeating the felting punch or stitch provides a felt 10 with bioresorbable polymer 14 covering a single surface or both surfaces of the collagen substrate 12.

Selection of the felting needle may influence the final porosity of the collagen substrate 12. Needles may be selected for shaft type (conical, square, star, or triangular), gauge, and the number of barbs on the needle. For example, a felt 10 created with a 20-gauge needle has a greater pore size after the bioresorbable polymer 14 resorbs, as compared to the pore size created by a 32-gauge needle. The pores and indentations created by the shaft shape and barbs may be exploited to maximize tissue ingrowth and thereby increase the strength of the implant in the body. The needle barb number, needle gauge size, the placement of the bioresorbable polymer 14 on the collagen substrate 12, and the extent of the punching process may be altered to provide a tight felt 10 with closely felted fibers.

After the felting process, the felt 10 may be treated to increase compatibility in the body. The felt 10 may be sterilized using radiation, for example. Agents to increase ingrowth of tissues into the collagen substrate 12 may also be applied to the felt 10, such as nutrient factors, growth factors, antimicrobials, anti-inflammatory agents, blood products, autologous or allogeneic differentiated cells, autologous or allogeneic undifferentiated or stem cells, and mixtures thereof.

Figure 3:
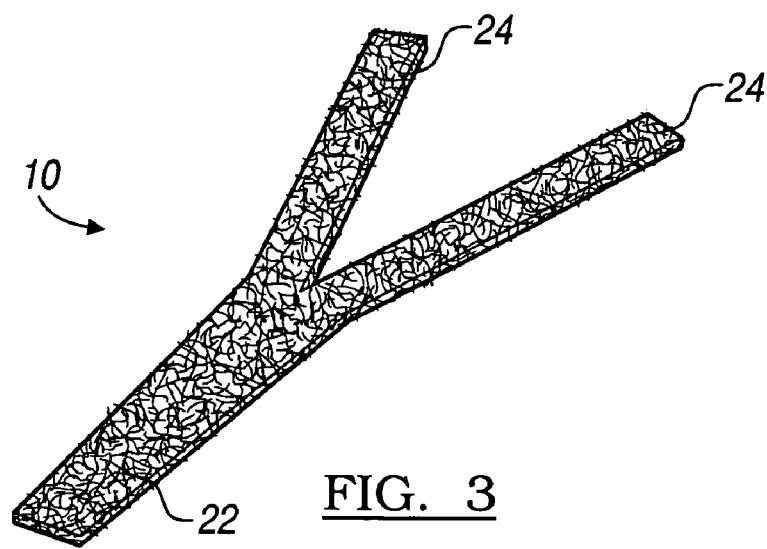
FIG. 3 depicts a bifurcated felt according to embodiments of the present invention.
Figure 4A:
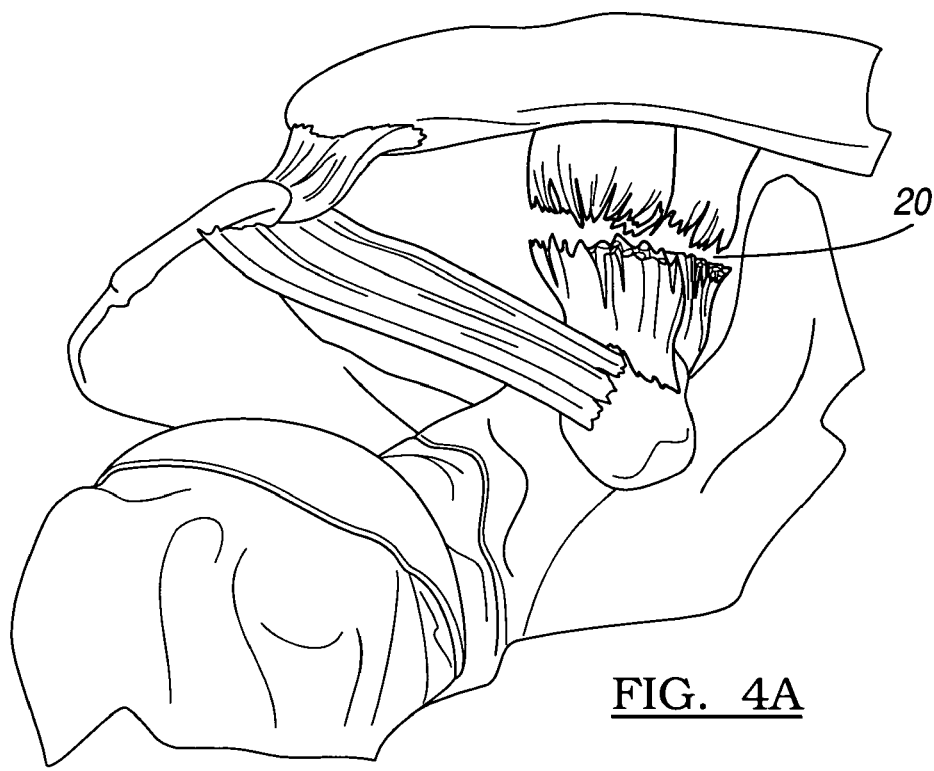
FIGS. 4A-4B depict a torn coracoclavicular ligament repaired with a felt according to embodiments of the present invention.
Figure 4B:
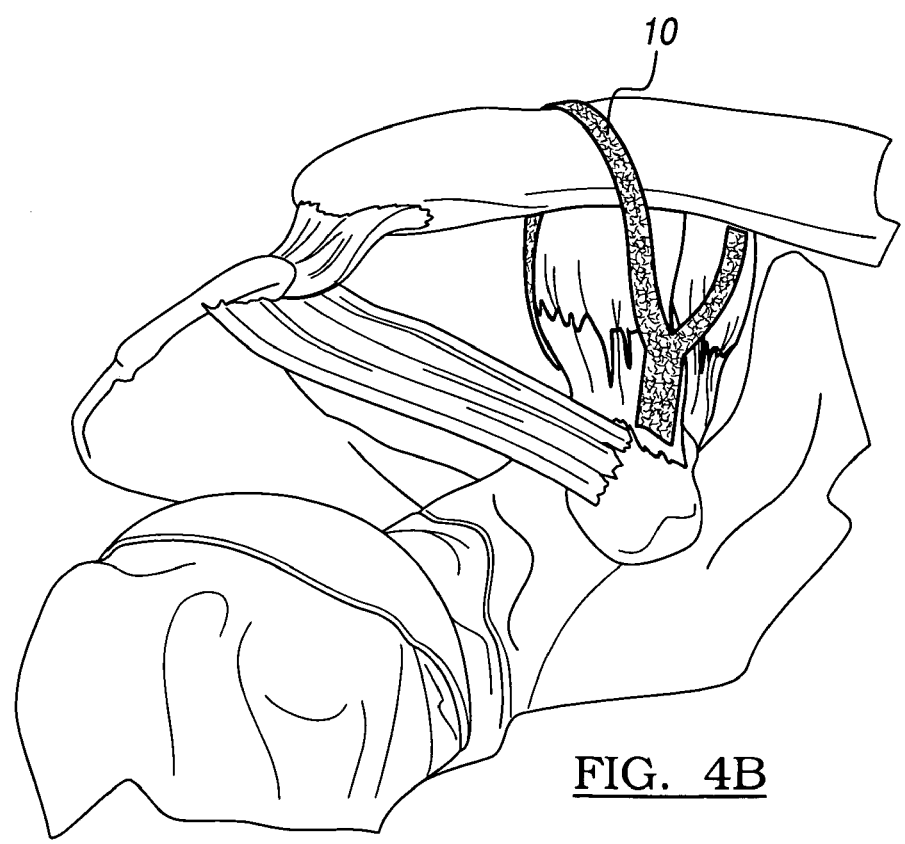

Various embodiments of the present invention may be used to augment a site in need of soft tissue repair 20. The felts 10 of embodiments of the invention are placed at a site in need of soft tissue repair 20. If needed, the felts 10 may be shaped prior to use. For example, the felt 10 may be shaped into a bifurcated strip having a base 22 and prongs 24, as depicted in FIG. 3. The bifurcated shape (or trifurcated, etc.) may be useful in augmenting sites by attaching the base 22 to one area in need of repair 20 and the prongs 24 to another area in need of repair 20 or by looping at least one of the prongs 24 around the site in need of repair 20. As depicted in FIG. 4A, an injury to the acromioclavicular ligament, coracoclavicular ligament, or the coracoacromial ligaments in the shoulder may cause displacement of the clavicle. A bifurcated felt 10 of the present invention may be used to reduce the clavicle to the appropriate level by attaching the base 22 to the coracoid process and attaching the prongs 24 to the coracoclavicular ligament. The prongs 24 may also be looped around the clavicle or in the case of the clavicle having a drill hole therein (not depicted), looped through the clavicle to reduce it to the appropriate level. The felt 10 may be attached using any suitable attachment means such as sutures, screws, staples, etc.

Figure 5A:
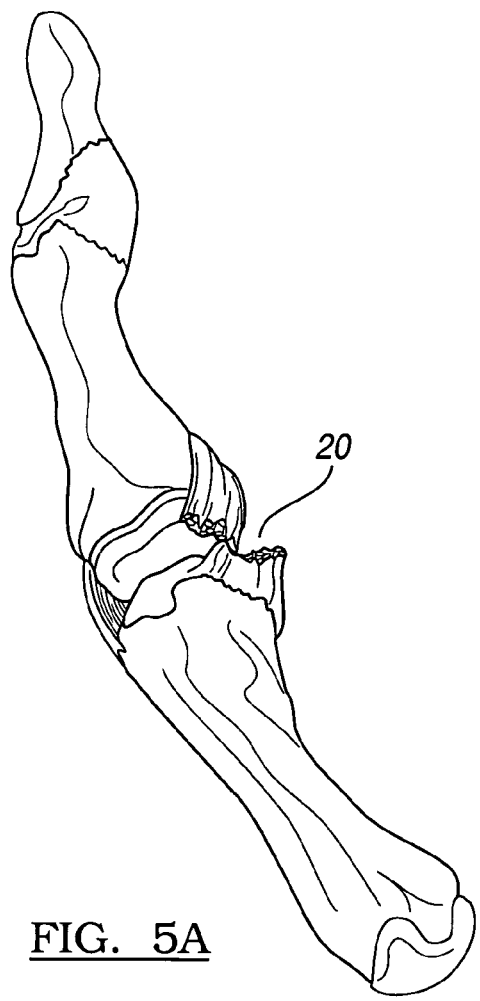
FIGS. 5A-5B depict a torn ulnar collateral ligament repaired with a felt according to embodiments of the present invention.
Figure 5B:
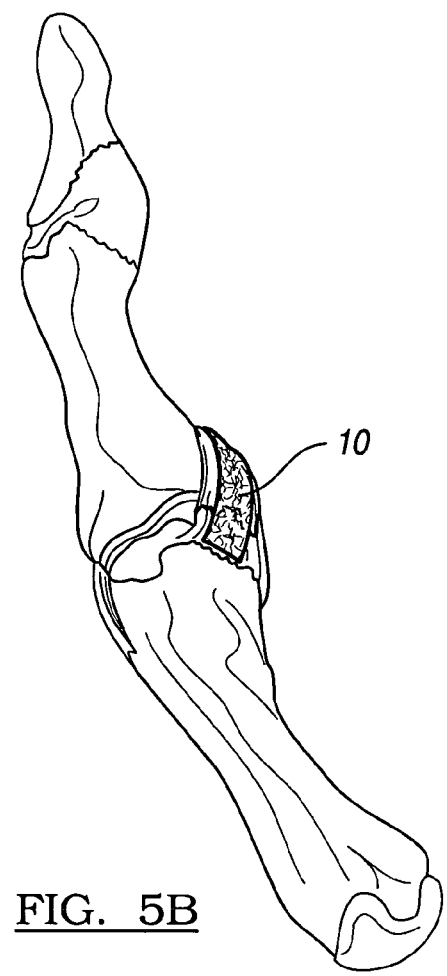
Figure 6A:
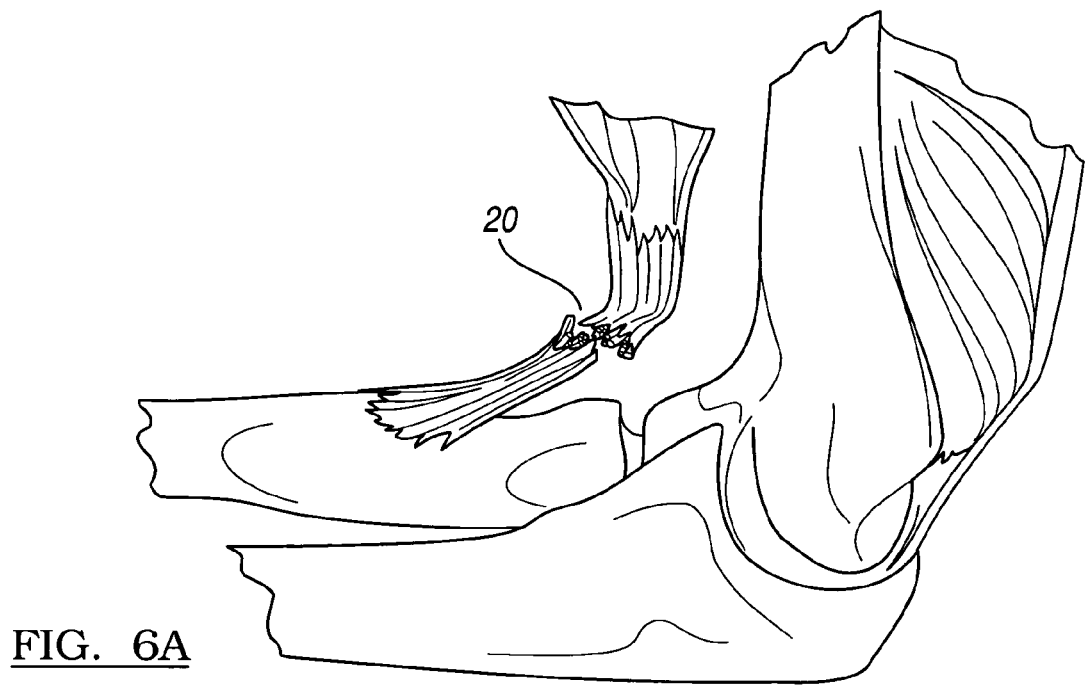
FIGS. 6A-6B depict a torn biceps tendon repaired with a felt according to embodiments of the present invention.
Figure 6B:
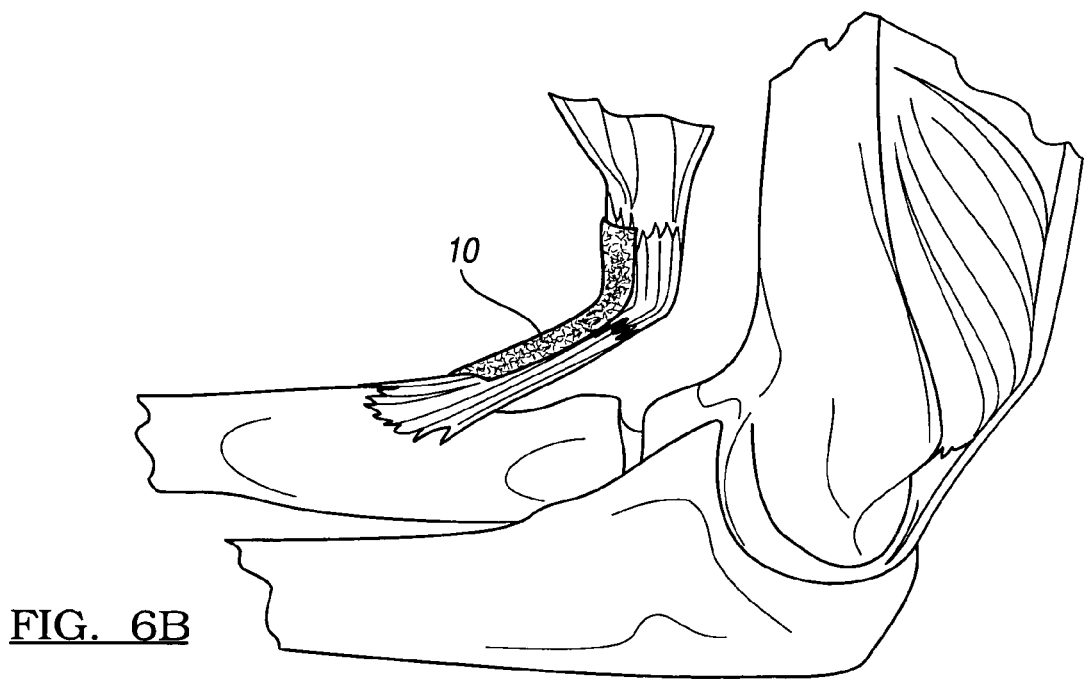

The methods may also be used in other regions of the body. Referring to FIGS. 5A and 5B, the site in need of repair 20 is a torn ulnar collateral ligament of the thumb. In such an embodiment a small felt 10 may be used to create a bridge between the torn tissues. As depicted in FIGS. 6A and 6B, the site in need of repair 20 is a torn biceps tendon which may also be repaired with the felt 10 bridging the two torn pieces of the biceps tendon. It is understood that the methods of the present invention may be employed in various areas of the body, including knees, wrists, ankles, etc.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A felt for repairing cartilage, ligament, or tendon soft tissue defects, comprising:
   a. a membranous collagen substrate; and
   b. a bioresorbable material felted onto said collagen substrate;
   wherein the bioresorbable material is selected from a synthetic polymer, a natural polymer, a polysaccharide, or combinations thereof;
   further wherein the synthetic polymer is selected from the group consisting of: polymers and co-polymers of glycolic acid, L-lactic acid, D-lactic acid, urethane urea, trimethylene carbonate, dioxanone, caprolactone, hydroxybutyrate, orthoesters, orthocarbonates, aminocarbonates, and physical combinations thereof; the natural polymer is selected from the group consisting of: elastin, silk, fibrin, fibrinogen, and mixtures thereof; and the polysaccharide is selected from the group consisting of: hyaluronic acid, chitin, chitosan, alginate, carboxymethylcellulose, and mixtures thereof.

2. The felt according to claim 1, wherein said collagen substrate is selected from the group consisting of: a xenograft source, an allograft source, a synthetic source, and mixtures thereof.

3. The felt according to claim 1, wherein said collagen substrate is from a porcine source.

4. The felt according to claim 1, wherein said collagen substrate is uncrosslinked.

5. The felt according to claim 1, wherein said collagen substrate is from about 1% to about 100% crosslinked.

6. The felt according to claim 1, wherein said collagen substrate is about 85% crosslinked to be substantially non-resorbable.

7. The felt according to claim 1, wherein said collagen substrate is substantially non-immunogenic.

8. A felt for repairing soft tissue defects, comprising:
   a. a membranous collagen substrate; and
   b. a bioresorbable material felted onto said collagen substrate, wherein the bioresorbable material comprises a polysaccharide selected from the group consisting of: hyaluronic acid, chitin, chitosan, alginate, carboxymethylcellulose, and mixtures thereof.

9. The felt according to claim 1, further comprising an agent incorporated into said felt, said agent selected from the group consisting of: nutrient factors, growth factors, antimicrobials, anti-inflammatory agents, blood products, autologous or allogeneic differentiated cells, autologous or allogeneic undifferentiated stem cells, and mixtures thereof.

10. A method of preparing a felt, comprising:
    a. providing a membranous collagen substrate; and
    b. felting a bioresorbable polymer in the form of a batting, web, or thread onto said substrate with a needle to pass said non-collagen bioresorbable polymer through said membranous collagen substrate;
    wherein the bioresorbable material is selected from a synthetic polymer, a natural polymer, a polysaccharide, or combinations thereof;
    further wherein the synthetic polymer is selected from the group consisting of: polymers and co-polymers of glycolic acid, L-lactic acid, D-lactic acid, urethane urea, trimethylene carbonate, dioxanone, caprolactone, hydroxybutyrate, orthoesters, orthocarbonates, aminocarbonates, and physical combinations thereof; the natural polymer is selected from the group consisting of: elastin, silk, fibrin, fibrinogen, and mixtures thereof; and the polysaccharide is selected from the group consisting of: hyaluronic acid, chitin, chitosan, alginate, carboxymethylcellulose, and mixtures thereof.

11. The method according to claim 10, further comprising crosslinking said membranous collagen using a technique selected from the group consisting of: chemical crosslinking, UV radiation, dehydrothermal crosslinking, and combinations thereof.

12. The method according to claim 11, wherein said chemical crosslinking is performed with a chemical crosslinking agent selected from the group consisting of: carbodiimide, glutaraldehyde, formaldehyde, diisocyanates, and mixtures thereof.

13. The method according to claim 10, said felting further comprising passing a barbed needle through said bioresorbable polymer and said collagen substrate to pass said bioresorbable polymer through at least one surface of said collagen substrate.

14. The method according to claim 10, further comprising sterilizing said felt after said felting.

15. The method according to claim 10, further comprising treating the felt with an agent selected from the group consisting of: nutrient factors, growth factors, antimicrobials, anti-inflammatory agents, blood products, autologous or allogeneic differentiated cells, autologous or allogeneic undifferentiated stem cells, and mixtures thereof.

16. A method of augmenting a cartilage, ligament, or tendon site in need of soft tissue repair, comprising:
 a. providing a felt, comprising a membranous collagen substrate and a non-collagen bioresorbable polymer felted onto said substrate; and
 b. placing said felt at said site in need of soft tissue repair;
 wherein the bioresorbable material is selected from a synthetic polymer, a natural polymer, a polysaccharide, or combinations thereof;
 further wherein the synthetic polymer is selected from the group consisting of: polymers and co-polymers of glycolic acid, L-lactic acid, D-lactic acid, urethane urea, trimethylene carbonate, dioxanone, caprolactone, hydroxybutyrate, orthoesters, orthocarbonates, aminocarbonates, and physical combinations thereof; the natural polymer is selected from the group consisting of: elastin, silk, fibrin, fibrinogen, and mixtures thereof; and the polysaccharide is selected from the group consisting of: hyaluronic acid, chitin, chitosan, alginate, carboxymethylcellulose, and mixtures thereof.

17. The method according to claim 16, further comprising preparing the felt to a predetermined shape.

18. The method according to claim 16, further comprising affixing said felt to the site in need of soft tissue repair.

* * * * *

UNITED STATES PATENT AND TRADEMARK OFFICE
CERTIFICATE OF CORRECTION

PATENT NO. : 7,252,832 B1  
APPLICATION NO. : 11/010836  
DATED : August 7, 2007  
INVENTOR(S) : Kevin Stone et al.

Page 1 of 1

It is certified that error appears in the above-identified patent and that said Letters Patent is hereby corrected as shown below:

Column 4, Line 33:    insert --of-- after "portion"

Column 4, Line 44:    "collage" should be --collagen--

Signed and Sealed this

Sixteenth Day of June, 2009

JOHN DOLL  
*Acting Director of the United States Patent and Trademark Office*